(12) United States Patent
Smith

(10) Patent No.: US 8,986,318 B2
(45) Date of Patent: Mar. 24, 2015

(54) PEDICLE DEPTH MEASURING APPARATUS

(76) Inventor: Jeffrey Scott Smith, Granbury, TX (US)

(*) Notice: Subject to any disclaimer, the term of this patent is extended or adjusted under 35 U.S.C. 154(b) by 0 days.

(21) Appl. No.: 13/427,865

(22) Filed: Mar. 22, 2012

(65) Prior Publication Data

US 2014/0171955 A1 Jun. 19, 2014

Related U.S. Application Data

(63) Continuation-in-part of application No. 13/427,841, filed on Mar. 22, 2012, which is a continuation-in-part of application No. 12/132,476, filed on Jun. 3, 2008, now Pat. No. 8,740,956.

(51) Int. Cl.
*A61B 17/88* (2006.01)
*A61B 19/00* (2006.01)

(52) U.S. Cl.
CPC ........... *A61B 19/46* (2013.01); *A61B 2019/461* (2013.01); *A61B 2019/462* (2013.01); *A61B 2019/5466* (2013.01)
USPC ............................ 606/102; 606/279; 600/594

(58) Field of Classification Search
USPC .................. 606/102, 130, 279; 600/587, 594
See application file for complete search history.

(56) References Cited

U.S. PATENT DOCUMENTS

| 3,499,222 | A | 3/1970 | Edelman et al. |
|---|---|---|---|
| 4,537,185 | A | 8/1985 | Stednitz |
| 4,858,601 | A | 8/1989 | Glisson |
| 5,019,079 | A * | 5/1991 | Ross .............................. 606/312 |
| 5,324,199 | A | 6/1994 | Brånemark |
| 5,989,025 | A | 11/1999 | Conley |
| 6,015,937 | A | 1/2000 | Brånemark |
| 6,033,438 | A | 3/2000 | Bianchi et al. |
| 6,053,916 | A | 4/2000 | Moore |
| 6,174,330 | B1 | 1/2001 | Stinson |
| 6,224,598 | B1 | 5/2001 | Jackson |
| 6,280,442 | B1 | 8/2001 | Barker |
| 6,302,888 | B1 | 10/2001 | Mellinger |
| 6,440,137 | B1 | 8/2002 | Horvath |
| 6,443,953 | B1 | 9/2002 | Perra |
| 6,565,567 | B1 | 5/2003 | Haider |
| 6,755,829 | B1 | 6/2004 | Bono |

(Continued)

OTHER PUBLICATIONS

U.S. Appl. No. 12/132,476, filed Jun. 30, 2008, Smith.

(Continued)

*Primary Examiner* — Todd Manahan
*Assistant Examiner* — Jessica Weiss
(74) *Attorney, Agent, or Firm* — Workman Nydegger

(57) ABSTRACT

A method for measuring the depth for installing a pedicle screw comprises utilizing a pedicle depth measuring apparatus which comprises an outer tubular member comprising a first end and a second end. A head member is joined to the second end. The head member comprises a base surface comprising an opening. An inner member is slidable within the outer tubular member. The inner member comprises a first end and a second end, the second end being slidable through the opening. The second end further comprises a marker disposed at a distal end. The marker comprises a material that is radiographically distinguishable, in which a placement of the marker within a cannulation of a patient's pedicle is observable. An indicator member is operable for indicating a distance between the marker and the base surface, in which the distance indicates a choice of a size of a pedicle screw for mitigating damage to the patient's nerve root.

4 Claims, 8 Drawing Sheets

(56) References Cited

U.S. PATENT DOCUMENTS

| | | |
|---|---|---|
| 6,921,403 B2 | 7/2005 | Cragg et al. |
| 7,235,076 B2 * | 6/2007 | Pacheco ............... 606/86 A |
| 7,294,128 B2 | 11/2007 | Alleyne |
| 7,871,413 B2 | 1/2011 | Park |
| 7,967,850 B2 | 6/2011 | Jackson |
| 8,016,866 B2 | 9/2011 | Warnick |
| RE44,268 E | 6/2013 | Kambin |
| 8,740,956 B2 | 6/2014 | Smith |
| 2002/0038123 A1 | 3/2002 | Visotsky et al. |
| 2004/0220567 A1 | 11/2004 | Eisermann et al. |
| 2005/0113929 A1 | 5/2005 | Cragg et al. |
| 2005/0203523 A1 * | 9/2005 | Wenstrom et al. ............ 606/79 |
| 2005/0261695 A1 | 11/2005 | Cragg et al. |
| 2005/0277918 A1 | 12/2005 | Shah et al. |
| 2006/0271196 A1 | 11/2006 | Saal et al. |
| 2006/0276788 A1 | 12/2006 | Berry et al. |
| 2007/0055232 A1 * | 3/2007 | Colquhoun ............... 606/54 |
| 2008/0287959 A1 * | 11/2008 | Quest et al. ............ 606/102 |
| 2009/0036934 A1 | 2/2009 | Biedermann |
| 2009/0198280 A1 | 8/2009 | Spratt |
| 2014/0148853 A1 | 5/2014 | Smith |
| 2014/0214099 A1 | 7/2014 | Smith |

OTHER PUBLICATIONS

U.S. Appl. No. 14/256,742, filed Apr. 18, 2014, Smith.
U.S. Appl. No. 13/427,841, filed Mar. 22, 2012, Smith.
U.S. Appl. No. 12/132,476, Jan. 18, 2011, Office Action.
U.S. Appl. No. 12/132,476, Jun. 22, 2011, Final Office Action.
U.S. Appl. No. 12/132,476, Sep. 24, 2013, Office Action.
U.S. Appl. No. 12/132,476, Jan. 24, 2014, Notice of Allowance.
U.S. Appl. No. 13/427,841, May 30, 2014, Restriction Requirement.
U.S. Appl. No. 13/427,841, Jun. 17, 2014, Office Action.

* cited by examiner

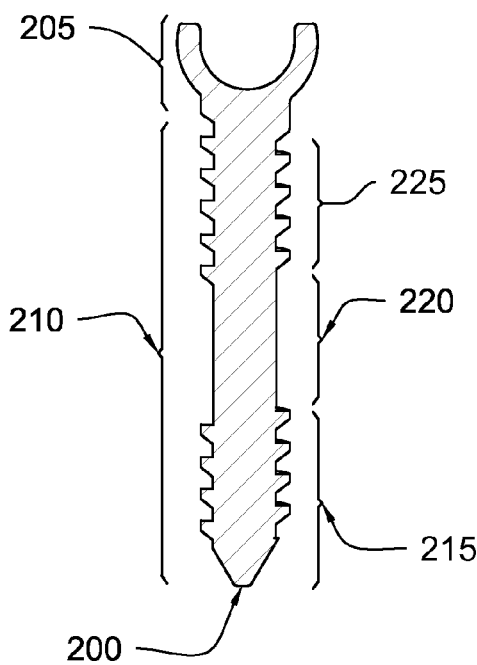
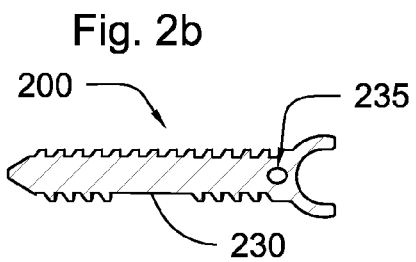
Fig. 2b
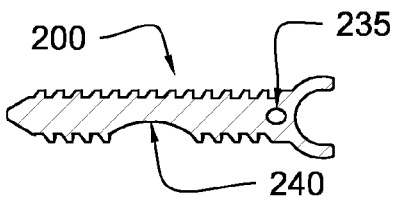
Fig. 2c
Fig. 2a
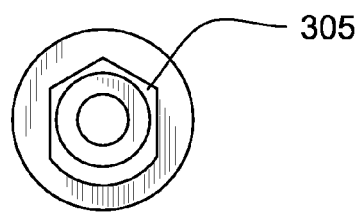
Fig. 3

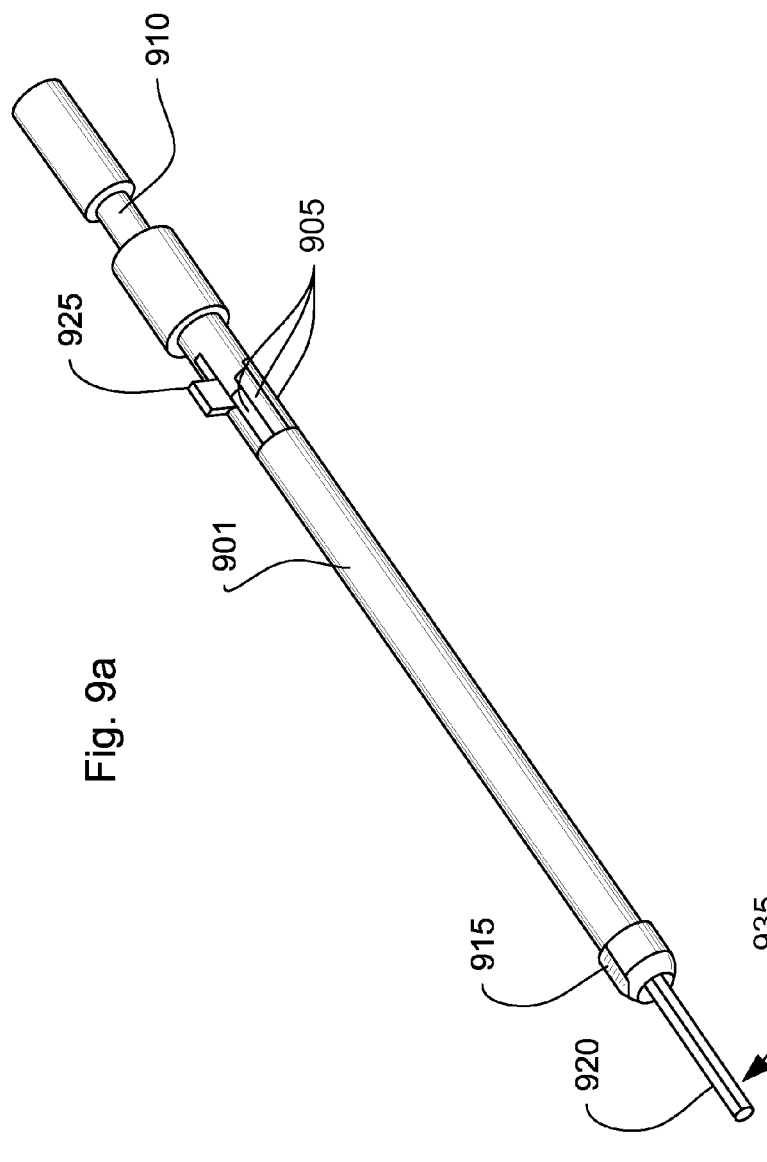
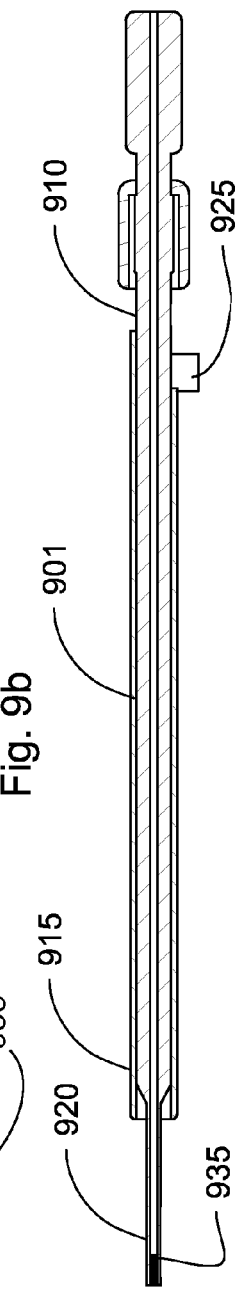

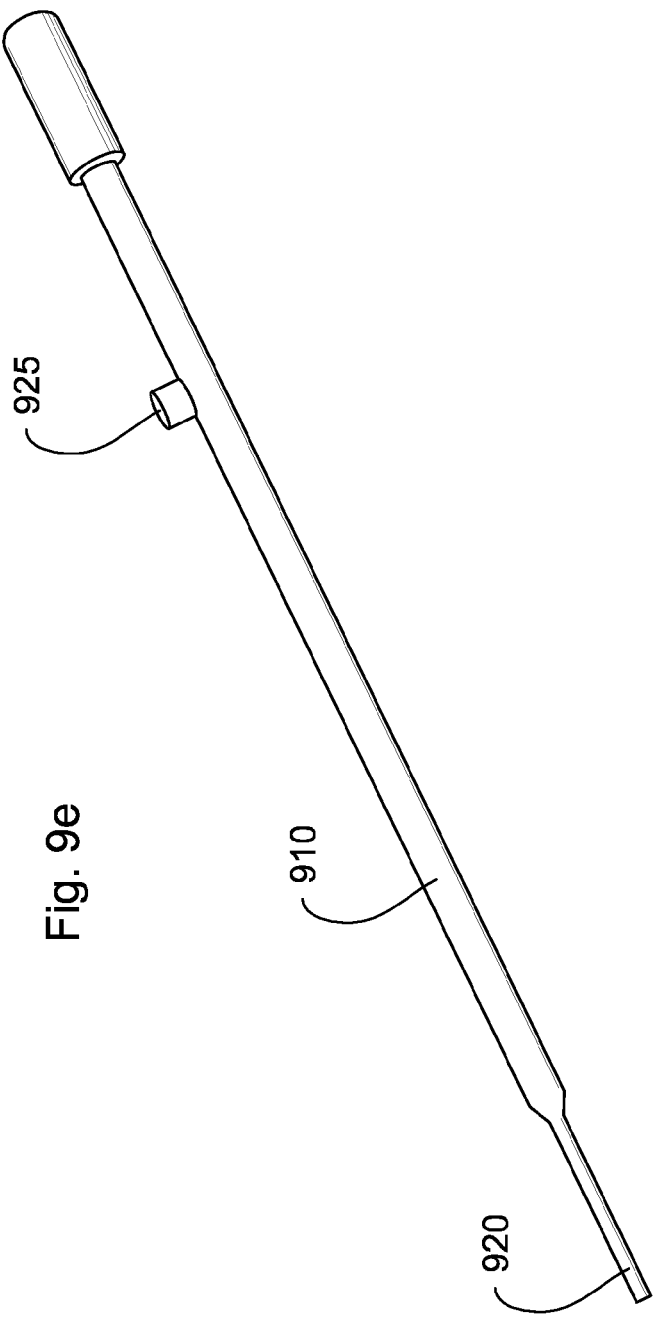

PEDICLE DEPTH MEASURING APPARATUS

CROSS-REFERENCE TO RELATED APPLICATIONS

The present utility patent application is a continuation-in-part application of U.S. patent application Ser. No. 12/132,476 filed Jun. 3, 2008 under 35 U.S.C. 111(a) (now U.S. Pat. No. 8,740,956 and also is a continuation-in-part application of U.S. patent application Ser. No. 12/132,476, filed Jun. 3, 2008, now U.S. Pat. No. 8,740,956, both under 35 U.S.C. 111(a). The contents of these related utility patent application are incorporated herein by reference for all purposes to the extent that such subject matter is not inconsistent herewith or limiting hereof.

FEDERALLY SPONSORED RESEARCH OR DEVELOPMENT

Not applicable.

REFERENCE TO SEQUENCE LISTING, A TABLE, OR A COMPUTER LISTING APPENDIX

Not applicable.

COPYRIGHT NOTICE

A portion of the disclosure of this patent document contains material that is subject to copyright protection. The copyright owner has no objection to the facsimile reproduction by anyone of the patent document or patent disclosure as it appears in the Patent and Trademark Office, patent file or records, but otherwise reserves all copyright rights whatsoever.

FIELD OF THE INVENTION

One or more embodiments of the invention generally relate to medical devices. More particularly, one or more embodiments of the invention relate to a modified pedicle screw system.

BACKGROUND OF THE INVENTION

The following background information may present examples of specific aspects of the prior art (e.g., without limitation, approaches, facts, or common wisdom) that, while expected to be helpful to further educate the reader as to additional aspects of the prior art, is not to be construed as limiting the present invention, or any embodiments thereof, to anything stated or implied therein or inferred thereupon. It is believed that spine surgery has become a major field in medicine over the past decades. Because the spine generally provides support and movement for the body, a problem with the spine (e.g., a back disorder) can disrupt even the simplest activities of life. In general, thousands of surgical fusions of the spine are performed each year in an attempt to decrease pain and increase function. Stabilization of the spine may be accomplished in a variety of way including, without limitation, the use of pedicle screws. A pedicle screw is generally a biocompatible screw that is typically inserted into a vertebra at the pedicle, which is a projection from the body of the vertebra that connects the body of the vertebra to the arch of the vertebra. Vertebrae generally have two pedicles.

By way of educational background, an aspect of the prior art generally useful to be aware of is that complications from the use of pedicles screws may occur, which may include, without limitation, loosening of screws, breakage of screws, damage to nearby joints, penetration of major blood vessels, and injuries to delicate neurological structures such as, but not limited to, nerve roots and the spinal cord. Typically, each level of the spine has an associated nerve root which is located just medial and inferior to the pedicle. The nerve root is typically in intimate contact with the pedicle through which the screw passes. If the pedicle screw violates the inferior or medial wall of the pedicle during placement, there may be potential for nerve root injury which may result in pain and/or dysfunction. Patients with nerves that have been damaged by poorly placed pedicle screws may fail to recover and may suffer from chronic and disabling pain. The nerve roots may be injured at the time of surgery, or injury may accumulate over time from the threads of the screws acting against the nerve roots. Due to the potential to damage the nerve roots if the threading of a pedicle screw interacts with the nerve root, proper installation of the pedicle screw is generally a concern in procedures involving pedicle screws.

By way of educational background, another aspect of the prior art generally useful to be aware of is that technology has been introduced over the years in an attempt to decrease the risk of nerve damage associated with placement of pedicle screws. For example, without limitation, one prior art system uses a method of determining the size and trajectory of a pedicle screw through 3D imaging. Also, the use of intraoperative fluoroscopy can reduce the incidence of misplaced screws, as can technology which utilizes computer guidance based on preoperative CT scanning. Even with these technologies, injury to nerve roots may result from the use of pedicle screw fixation.

The facet joints of the spine located between vertebrae are frequently a problem when placing pedicle screws. It is typically desired to preserve the facet joints above a fusion, if possible, during placement of pedicle screws. Injury to the facet joints can lead to chronic pain and the need for additional intervention, including, without limitation, surgery. The relative interaction between facet joints and the heads of implanted pedicle screws varies with the size and shape of these joints, as well as with the relationship of the screw to the entrance point and course of the pedicle. These, and other factors, may make it difficult for the surgeon to know exactly where the head of the pedicle screw will finally rest after insertion.

In view of the foregoing, it is clear that these traditional techniques are not perfect and leave room for more optimal approaches.

BRIEF DESCRIPTION OF THE DRAWINGS

The present invention is illustrated by way of example, and not by way of limitation, in the figures of the accompanying drawings and in which like reference numerals refer to similar elements and in which:

FIGS. 2a through 2c illustrate cross sectional views of pedicle screws, in accordance with various embodiments of the present invention;

FIG. 3 is a diagrammatic top view of an exemplary modified pedicle screw, in accordance with an embodiment of the present invention;

FIGS. 9a through 9e illustrate an exemplary device for determining the distance from a pedicle screw head to a nerve root, in accordance with an embodiment of the present invention. FIG. 9a is a side perspective view. FIG. 9b is a cross sectional side view. FIG. 9c is a side perspective view of an external housing. FIG. 9d is a side perspective view of length guides on the external housing, and FIG. 9e is a side perspective view of an internal tapered conduit.

Figure 1:
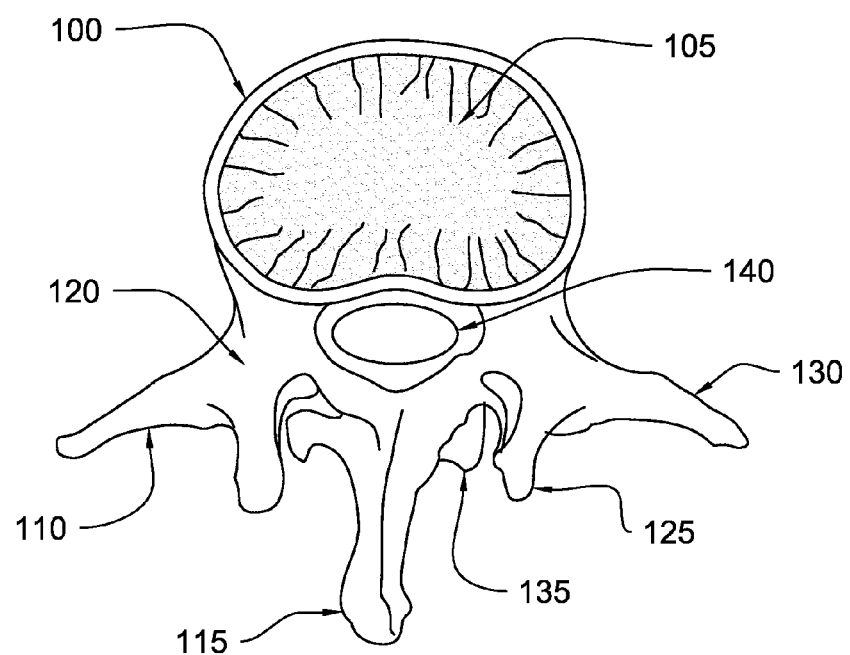
FIG. 1 is an illustration of a vertebra in transverse cross section.

Unless otherwise indicated illustrations in the figures are not necessarily drawn to scale.

DETAILED DESCRIPTION OF SOME EMBODIMENTS

Embodiments of the present invention are best understood by reference to the detailed figures and description set forth herein.

Embodiments of the invention are discussed below with reference to the Figures. However, those skilled in the art will readily appreciate that the detailed description given herein with respect to these figures is for explanatory purposes as the invention extends beyond these limited embodiments. For example, it should be appreciated that those skilled in the art will, in light of the teachings of the present invention, recognize a multiplicity of alternate and suitable approaches, depending upon the needs of the particular application, to implement the functionality of any given detail described herein, beyond the particular implementation choices in the following embodiments described and shown. That is, there are numerous modifications and variations of the invention that are too numerous to be listed but that all fit within the scope of the invention. Also, singular words should be read as plural and vice versa and masculine as feminine and vice versa, where appropriate, and alternative embodiments do not necessarily imply that the two are mutually exclusive.

It is to be further understood that the present invention is not limited to the particular methodology, compounds, materials, manufacturing techniques, uses, and applications, described herein, as these may vary. It is also to be understood that the terminology used herein is used for the purpose of describing particular embodiments only, and is not intended to limit the scope of the present invention. It must be noted that as used herein and in the appended claims, the singular forms "a," "an," and "the" include the plural reference unless the context clearly dictates otherwise. Thus, for example, a reference to "an element" is a reference to one or more elements and includes equivalents thereof known to those skilled in the art. Similarly, for another example, a reference to "a step" or "a means" is a reference to one or more steps or means and may include sub-steps and subservient means. All conjunctions used are to be understood in the most inclusive sense possible. Thus, the word "or" should be understood as having the definition of a logical "or" rather than that of a logical "exclusive or" unless the context clearly necessitates otherwise. Structures described herein are to be understood also to refer to functional equivalents of such structures. Language that may be construed to express approximation should be so understood unless the context clearly dictates otherwise.

Unless defined otherwise, all technical and scientific terms used herein have the same meanings as commonly understood by one of ordinary skill in the art to which this invention belongs. Preferred methods, techniques, devices, and materials are described, although any methods, techniques, devices, or materials similar or equivalent to those described herein may be used in the practice or testing of the present invention. Structures described herein are to be understood also to refer to functional equivalents of such structures. The present invention will now be described in detail with reference to embodiments thereof as illustrated in the accompanying drawings.

From reading the present disclosure, other variations and modifications will be apparent to persons skilled in the art. Such variations and modifications may involve equivalent and other features which are already known in the art, and which may be used instead of or in addition to features already described herein.

Although Claims have been formulated in this application to particular combinations of features, it should be understood that the scope of the disclosure of the present invention also includes any novel feature or any novel combination of features disclosed herein either explicitly or implicitly or any generalization thereof, whether or not it relates to the same invention as presently claimed in any Claim and whether or not it mitigates any or all of the same technical problems as does the present invention.

Features which are described in the context of separate embodiments may also be provided in combination in a single embodiment. Conversely, various features which are, for brevity, described in the context of a single embodiment, may also be provided separately or in any suitable subcombination. The Applicants hereby give notice that new Claims may be formulated to such features and/or combinations of such features during the prosecution of the present application or of any further application derived therefrom.

References to "one embodiment," "an embodiment," "example embodiment," "various embodiments," etc., may indicate that the embodiment(s) of the invention so described may include a particular feature, structure, or characteristic, but not every embodiment necessarily includes the particular feature, structure, or characteristic. Further, repeated use of the phrase "in one embodiment," or "in an exemplary embodiment," do not necessarily refer to the same embodiment, although they may.

As is well known to those skilled in the art many careful considerations and compromises typically must be made when designing for the optimal manufacture of a commercial implementation any system, and in particular, the embodiments of the present invention. A commercial implementation in accordance with the spirit and teachings of the present invention may configured according to the needs of the particular application, whereby any aspect(s), feature(s), function(s), result(s), component(s), approach(es), or step(s) of the teachings related to any described embodiment of the present invention may be suitably omitted, included, adapted, mixed and matched, or improved and/or optimized by those skilled in the art, using their average skills and known techniques, to achieve the desired implementation that addresses the needs of the particular application.

It is to be understood that any exact measurements/dimensions or particular construction materials indicated herein are solely provided as examples of suitable configurations and are not intended to be limiting in any way. Depending on the needs of the particular application, those skilled in the art will readily recognize, in light of the following teachings, a multiplicity of suitable alternative implementation details.

One or more embodiments of the present invention relate to a pedicle screw for use in spine surgery. In some embodiments this pedicle screw comprises a modification to the shaft of the pedicle screw involving the removal of the normal screw threading along a portion of the screw, thereby conceivably making the screw safer by generally reducing the potential for nerve root injury, as this non-threaded region is less likely to cause injury if the nerve passes against it. In some alternate embodiments, the modified portion of the shaft of the screw may be partially threaded rather than non-threaded. In addition to the modification of the threaded shaft, some embodiments may also comprise a system to control the rotation of the non-threaded portion of the shaft and the application of a radiographic marker to assess fluoroscopically the position of the non-threaded portion of the screw shank with relation to the anatomic structures of the spine. In order to achieve some of the benefits of the new pedicle screw in some embodiments, it is believed that it is advantageous for the non-threaded portion of the screw to be placed to both the proper depth and the proper rotation with respect to the associated nerve root with the non-threaded area of the screw aligned with and facing the nerve root after screw insertion.

FIG. 1 is an illustration of a vertebra in transverse cross section. Referring further to FIG. 1, a typical vertebra 101 is one of the bones comprising a human spine. The vertebra 100 has several components, a vertebral body 105, a vertebral foramen 110, a spinous process 115, a pedicle 120, a superior articular process 125, a transverse process 130, and a lamina 135. Two vertebral bodies combine to create the vertebral foremen 110 through which passes a nerve root and a spinal cord 140. The human spine varies widely across the population, and, accordingly, so does the pedicle 120. Because the pedicle 120 varies in its anatomy, biocompatible hardware must also be available in various shapes and sizes that is inserted into or otherwise affixed to the pedicle 120, for example a bone screw.

FIGS. 2a through 2c illustrate cross sectional views of pedicle screws, in accordance with various embodiments of the present invention. Referring further to FIG. 2a, the bone screw (e.g., a pedicle screw 200) has a head 205 and a shaft 210. And like any screw, the pedicle screw 200 has various characteristics, for example, without limitation, a length, a major diameter, a minor diameter, a thread pitch, and a taper profile that can all be adjusted given the various pedicle pathologies. The shaft 210 for example, without limitation, can have a major diameter of 6.5 mm, a length of 40 mm, and a thread pitch of 3.0 mm, with other measurements contemplated so that the pedicle screw 200 performs as intended. The pedicle screw 200 has a first threaded shaft portion 215, a middle shaft portion 220, and a second threaded shaft portion 225. The second threaded shaft portion 225 is contiguous to the head 205, but alternatively there can be a shank or other portion disposed between the second threaded shaft portion 225 and the head 205. The middle shaft portion 220 is of an irregular form, which is to say, it does not share at least one of the same characteristics as the first threaded shaft portion 215 and the second threaded shaft portion 225. The pedicle screw 200 preferably has a major/minor diameter combination of cylindrical, so that the middle shaft portion 220 lacks any of the threading in the first and second threaded shaft portions 215, 225, respectively, and is of the cylindrical minor diameter. Any combination of cylindrical and tapered diameters are contemplated within this application, for example, without limitation, the minor diameter may be tapered and the major diameter cylindrical, in which case, the middle shaft portion 220 would have the tapered minor diameter. Other embodiments of the presently preferred embodiment are also contemplated, for example, without limitation, those described below.

Referring further to FIGS. 2b and 2c, the middle shaft portion 220 can be threaded along a portion, for example, without limitation, half of its cylindrical (or tapered) surface, generally shown at 230. In this embodiment a marker 235 is placed on the head 205 as a visual indicator of the location of the non-threaded minor diameter of the middle shaft portion 220. The marker 235 allows for the proper alignment of the pedicle screw 200 such that the threads of the middle shaft portion 220 are placed to minimize potential thread contact with the nerve root or spinal cord 140. Referring to FIG. 2c, the middle shaft portion 220 has a concave feature 240, for example. The concave feature 240 can be threaded, and is preferably threaded on the non-concave portion, so that when inserted into the pedicle 120, the pedicle screw 200 is aligned such that the concave feature 240 minimizes contact with the associated nerve root.

In practice, when pedicle screws are evenly placed with the assistance or the aid of intraoperative fluoroscopy and/or CT guided imaging techniques, for example, without limitation, there still exists the possibility of placement error that can go undetected resulting in nerve root damage and/or injury. Therefore, it is contemplated that the placement of the pedicle screw 200 directly addresses when these drilling errors are known so that the disclosed pedicle screw 200 will greatly lessen damage caused by the threads of prior art pedicle screws.

A number of embodiments have been described. It will be understood that various modifications may be made without departing from the spirit and scope of the presently preferred embodiment. For example, without limitation, the biocompatible material contemplated is titanium, but other biocompatible materials are also applicable. The middle shaft portion 220 can be fully threaded but with a smaller thread diameter, or with blunt edges to protect the nerve. Further, the middle shaft portion 220 can be rotated to turn the threads away from the foramen or away from the medial wall of the pedicle. Also, the head 205 can be rotatable for easy positioning and manipulation.

It is believed that it is generally important for a surgeon performing a procedure on a spine to be able to verify the placement of a modified pedicle screw according to an embodiment of the present invention after insertion of the screw. FIG. 3 is a diagrammatic top view of an exemplary modified pedicle screw, in accordance with an embodiment of the present invention. In the present embodiment, the head of the pedicle screw comprises a socket 305 into which a driver can only be inserted in one orientation. The non-threaded portion of the pedicle screw shaft is oriented with respect to the shape of socket 305 so that the non-threaded portion is aligned with an indicator on the driver when the driver is inserted into socket 305. The indicator on the opposite end of the driver generally enables a surgeon to easily determine the rotational orientation of the unthreaded portion of the pedicle screw even after the screw has been inserted into the pedicle. By correctly orienting the indicator on the driver, the surgeon can align the non-threaded portion of the screw towards the known position of the nerve root. In addition to this, the screw itself may comprise a marker on the shaft corresponding to the non-threaded portion of the screw, as shown by way of example in FIGS. 2b and 2c. This marker may be radiographically visible to generally enable a surgeon to see the marker and correctly position the non-threaded portion of the screw toward the nerve root when performing a procedure under fluoroscopy.

Some embodiments of the present invention may comprise a radiographic marker added to a pedicle screw system to allow an operating surgeon to assess the depth and position of a pedicle screw during insertion. The system typically uses a screw with a modified shaft where the threading has been removed, as illustrated by way of example in FIGS. 2a through 2c. The proper positioning of the screw typically places the unthreaded area of the screw at the depth of the nerve and facing the nerve after screw insertion. The marker generally enables a surgeon to properly assess the depth and location of the non-threaded portion of the screw and determine its relationship to the location of the nerve root while performing a spinal procedure. This may enable the surgeon to minimize potential interaction between the threads of the pedicle screw and the nerve root. One may expect that the addition of a marker may result in improved accuracy of screw placement. It is contemplated that a marker may be applied to virtually any type of screw for the purpose of determining the relative depth of placement with regard to anatomic structures. For example, without limitation, a marker may be made with the addition of a coating to the screw, as illustrated by way of example in FIG. 4. In another non-limiting example, as shown by way of example in FIG. 5, a marker is made of a single band or wire of material, which is radiographically visible, added to the unthreaded portion of the screw. Additionally, markers may be placed within the shaft of the screw, as illustrated by way of example in FIGS. 6 and 7.

Figure 4:
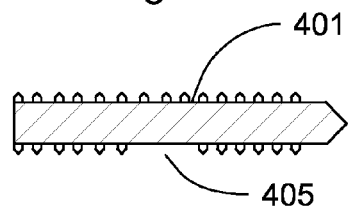
FIG. 4 is a diagrammatic side view of an exemplary integrated marker for assessing pedicle screw placement, in accordance with an embodiment of the present invention.

FIG. 4 is a diagrammatic side view of an exemplary integrated marker 401 for assessing pedicle screw placement, in accordance with an embodiment of the present invention. Marker 401 typically indicates the depth of a non-threaded portion 405 of the screw. In the present embodiment, marker 401 is incorporated into the screw by way of an external coating of additional material on or in line with the non-threaded portion 405 of the screw. This coating is typically made of a material which is contrasting to the material of the screw under fluoroscopy such as, but not limited to, various different metals such as gold, tantalum, etc. This enables marker 401 to generally be seen under fluoroscopy.

Figure 5:
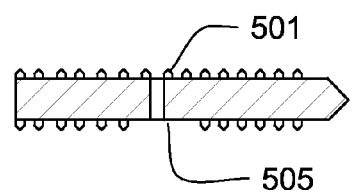
FIG. 5 is a diagrammatic side view of an exemplary integrated marker for assessing pedicle screw placement, in accordance with an embodiment of the present invention.

FIG. 5 is a diagrammatic side view of an exemplary integrated marker 501 for assessing pedicle screw placement, in accordance with an embodiment of the present invention. In the present embodiment, marker 501 is applied externally to a screw through the addition of a wire or band between the boundaries of a non-threaded portion 505 of the screw. In some alternate embodiments two bands or wires may be placed around the screw at the boundaries of the non-threaded portion of the screw to indicate the top and the bottom of the non-threaded portion of the screw. In the present embodiment, a small groove is included without limitation in the shaft of the screw in which the wire or band is placed to generally maintain a smooth surface on the screw, particularly at non-threaded portion 505. In some alternate embodiments, a wire or band may be placed around a screw without the use of a groove. In the present embodiment, marker 501 is made of a material which is contrasting to the material of the screw (i.e., radiographically visible).

Those skilled in the art will readily recognize, in light of and in accordance with the teachings of the present invention, that some alternate embodiments may use a multiplicity of suitable means for creating a marker on a pedicle screw. For example, without limitation, a marker may be produced by creating a geometrical clue to be seen under the fluoroscope, such as, but not limited to, a hole drilled in the shaft of the screw or a defect cut in the shaft of the screw. This method generally does not require the attachment of additional material to the shaft of the screw. In other alternate embodiments, an internal marker may be used. Internal markers may be placed in a screw by drilling into the screw and placing a metal that is dissimilar to the material of the screw or other contrasting material which provides a contrasting view under radiographic imaging into the hole created by the drilling. Internal markers may be solid for non-cannulated screws or may be drilled though for cannulated screws. A cannulated screw comprises a channel in the shaft to create a hollow or partially hollow screw.

Figure 6:
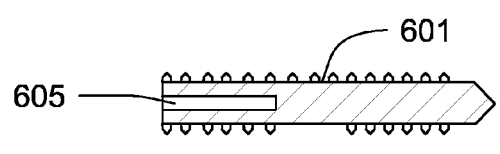
FIG. 6 is a cross sectional view of an exemplary internal marker for assessing pedicle screw placement, in accordance with an embodiment of the present invention.

FIG. 6 is a cross sectional view of an exemplary internal marker 601 for assessing pedicle screw placement, in accordance with an embodiment of the present invention. In the present embodiment, marker 601 is inserted into the shaft of a screw, which comprises a hole 605 that has been drilled to enable marker 601 to be inserted into the shaft of the screw. Hole 605 is drilled to a depth corresponding to a non-threaded portion 610 of the shaft of the screw so that marker 601 may be aligned with non-threaded portion 610.

Figure 7:
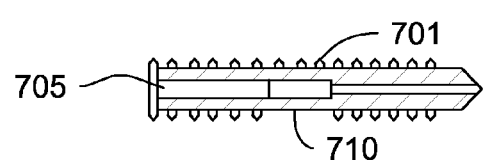
FIG. 7 is a cross sectional view of an exemplary internal marker for assessing pedicle screw placement, in accordance with an embodiment of the present invention.

FIG. 7 is a cross sectional view of an exemplary internal marker 701 for assessing pedicle screw placement, in accordance with an embodiment of the present invention. In the present embodiment, a screw is fully cannulated and comprises a hole 705 through the entire shaft of the screw. The diameter of hole 705 near the screw head is sized accordingly to allow placement of marker 701. Near the tip of the shaft of the screw, the diameter of hole 705 decreases to generally prevent marker 701 from migrating and to generally ensure proper placement of marker 701 during use in alignment with a non-threaded portion 710 of the screw.

The use of a marker such as, but not limited to, those illustrated by way of example in the foregoing embodiments generally enables a user to confirm after screw placement that the screw has been inserted to the proper depth to place the unthreaded portion of the screw in proper relation to the location of the nerve root. As described above, proper screw rotation is verified by a visual check of the indicator on the driver or on the screw. The ability to control both the depth and rotational orientation of the non-threaded portion of the modified screw generally enables a surgeon to minimize the risk of nerve root injury during screw placement. In addition to improving the accuracy of the placement of the unthreaded portion of the pedicle screw with regard to the nerve root, the addition of a marker may also enable the unthreaded portion of the screw to be made smaller because of this improved accuracy. The use of a smaller unthreaded portion enables the screw to have a greater portion of the shaft covered with threading, which may result in a screw with greater purchase and pull out strength as well as improved safety with regard to potential nerve root injury.

Figure 8:
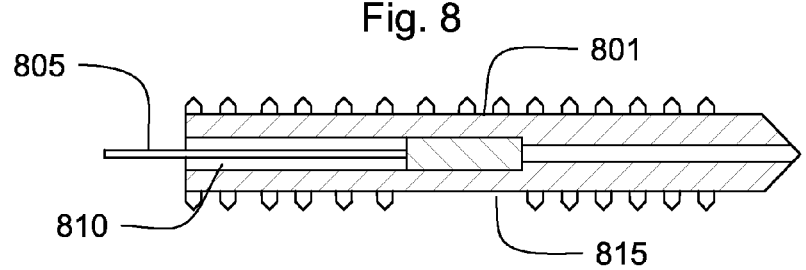
FIG. 8 is a cross sectional view of an exemplary removable marker for assessing pedicle screw placement, in accordance with an embodiment of the present invention.

FIG. 8 is a cross sectional view of an exemplary removable marker 801 for assessing pedicle screw placement, in accordance with an embodiment of the present invention. In the present embodiment, marker 801 is designed to be attached to the end of a wire 805. Wire 805 enables marker 801 to be placed inside a hole 810 in a screw after the insertion of the screw into a patient's pedicle. Wire 805 also enables marker 801 to be removed from hole 810 after verification of the depth of the screw. The screw is cannulated to the depth of an unthreaded portion 815 of the screw at a diameter into which marker 801 may be inserted. The remaining portion of the shaft of the screw is cannulated in a smaller diameter. In some alternate embodiments, the remaining portion of the shaft may not be cannulated. In the present embodiment, the length of marker 801 is equal to the length of unthreaded portion 815 of the screw. Fluoroscopy is used for verification of the placement of unthreaded portion 815.

In typical use of a pedicle screw system in accordance with an embodiment of the present invention, it is contemplated that the non-threaded portion of the pedicle screw should be inserted to a depth such that the non-threaded portion spans the nerve root. Some embodiments comprise two mechanisms to generally ensure that the screw is at the proper depth: measurement before insertion and verification after insertion. Prior to screw insertion, an estimate of the distance between the desired location of the pedicle screw head and the nerve root can be closely estimated with the use of a specially designed depth gauge which may be included, without limitation, in some embodiments. In general, the proper placement of pedicle screws traditionally has relied upon the surgeon being able to locate an acceptable entrance to the pedicle, for example, without limitation, by anatomic landmarks or by using fluoroscopic visualization. Once the entrance to the pedicle has been found, the pedicle is cannulated (i.e., a cavity is created for the pedicle screw) with the use of a separate instrument, such as, but not limited to, a pedicle finder or a threaded tap. After the course of the pedicle has been clearly identified, the pedicle screw is usually inserted. The pedicle screw generally passes through the pedicle, past the nerve root, and into the vertebral body. With the use of a pedicle screw system according to an embodiment of the present invention, a method to measure the distance from the presumed location of the head of the pedicle screw after installation and the associated nerve root may enable a surgeon to select a screw of an appropriate size for insertion. Previously, the distance between the base of the screw and the nerve root has typically not been measured.

Figure 9C:
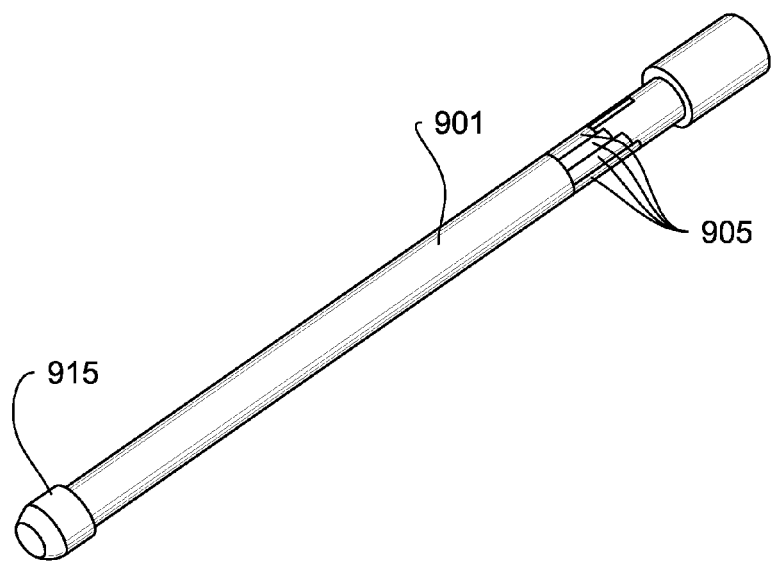
Figure 9D:
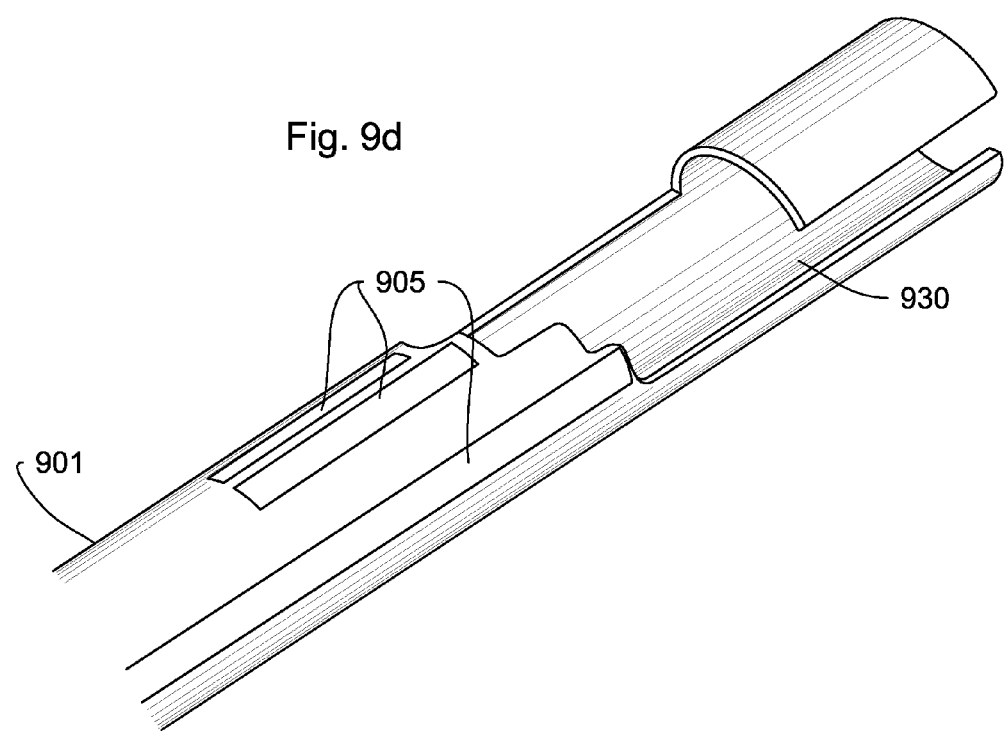

FIGS. 9a through 9e illustrate an exemplary depth gauge for measuring the distance from a pedicle screw head to a nerve root, in accordance with an embodiment of the present invention. FIG. 9a is a side perspective view. FIG. 9b is a cross sectional side view. FIG. 9c is a side perspective view of an external housing 901. FIG. 9d is a side perspective view of length guides 905 on external housing 901, and FIG. 9e is a side perspective view of an internal tapered conduit 910. In the present embodiment, the depth gauge generally enables a user to measure and confirm the distance from the base of a pedicle screw head to the associated nerve root. External housing 901 of the gauge comprises a pedicle screw head 915 or a similarly shaped object at one end for accurate measurement. By replicating or mimicking the size and shape of the head of the pedicle screw to be used in a procedure, screw head 915 generally ensures that the measurement obtained by the depth gauge is accurate. In some alternate embodiments in which screws with different types of heads are used or different types of attachment means such as, but not limited to, bolts or unthreaded pins are used, the housing may not comprise a pedicle screw head or may comprise an item other than a pedicle screw head. Referring to FIGS. 9a and 9b in the present embodiment, conduit 910 is inserted into housing 901 so that a tapered tip 920 projects from pedicle screw head 915. Conduit 910 is able to slide back and forth within housing 901. Referring to FIGS. 9a, 9b and 9e, conduit 910 comprises a measurement indicator 925 that corresponds to length guides 905 on housing 901.

Referring to FIG. 9d, when inserting conduit 910 into housing 901, indicator 925 may be slid through a slot 930 in housing 901 in order to reach length guides 905. Those skilled in the art will readily recognize, in light of and in accordance with the teachings of the present invention, that some alternate embodiments may comprise a multiplicity of suitable configurations for the indicators and guides such as, but not limited to, indicators that are integrated into the housing, dials, sliding indicators, lighted indicators, etc. In the present embodiment, length guides 905 step up at 5 mm increments. However, in some alternate embodiments, the length guides may step up at larger or smaller increments, for example, without limitation, 2.5 mm or 10 mm. In the present embodiment, referring to FIG. 9b, tip 920 of conduit 910 comprises an internal marker 935 that is made of a radio opaque material such as, but not limited to, tantalum. It is contemplated that in some alternate embodiments various different types of markers may be used such as, but not limited to, external coatings, bands or wires on the tip of the conduit. The device allows the surgeon to place a marker within the pedicle at various distances from the base of the pedicle screw head. The device allows for the distance between the base of the pedicle screw head 915 and the marker 935 to be adjusted incrementally until the marker 935 in the tip of the device is located in a position that spans the presumed location of the nerve root. In this manner, the surgeon is able to adjust the distance between the screw head 915 and the marker 935 until the optimal length is identified. Fluoroscopy is used to verify this relationship. In this particular embodiment, the marker 935 is designed to span across the location of the nerve root and is meant to correspond to the general location and length of the non-threaded portion 220 of the previously described pedicle screw. This measurement taken from the gauge by adjusting and visually confirming location of measurement indicator 925 as related to the measuring slots 905 is then used to select a corresponding pedicle screw for insertion. In other embodiments, the gauge may be used to measure the exact distance from the pedicle screw head 915 to the nerve root 1030. In this embodiment, the length of the marker could be much smaller, but large enough to be seen fluoroscopically, and would not need to be related to the length of the nonthreaded portion 220 of the pedicle screw.

Figure 10:
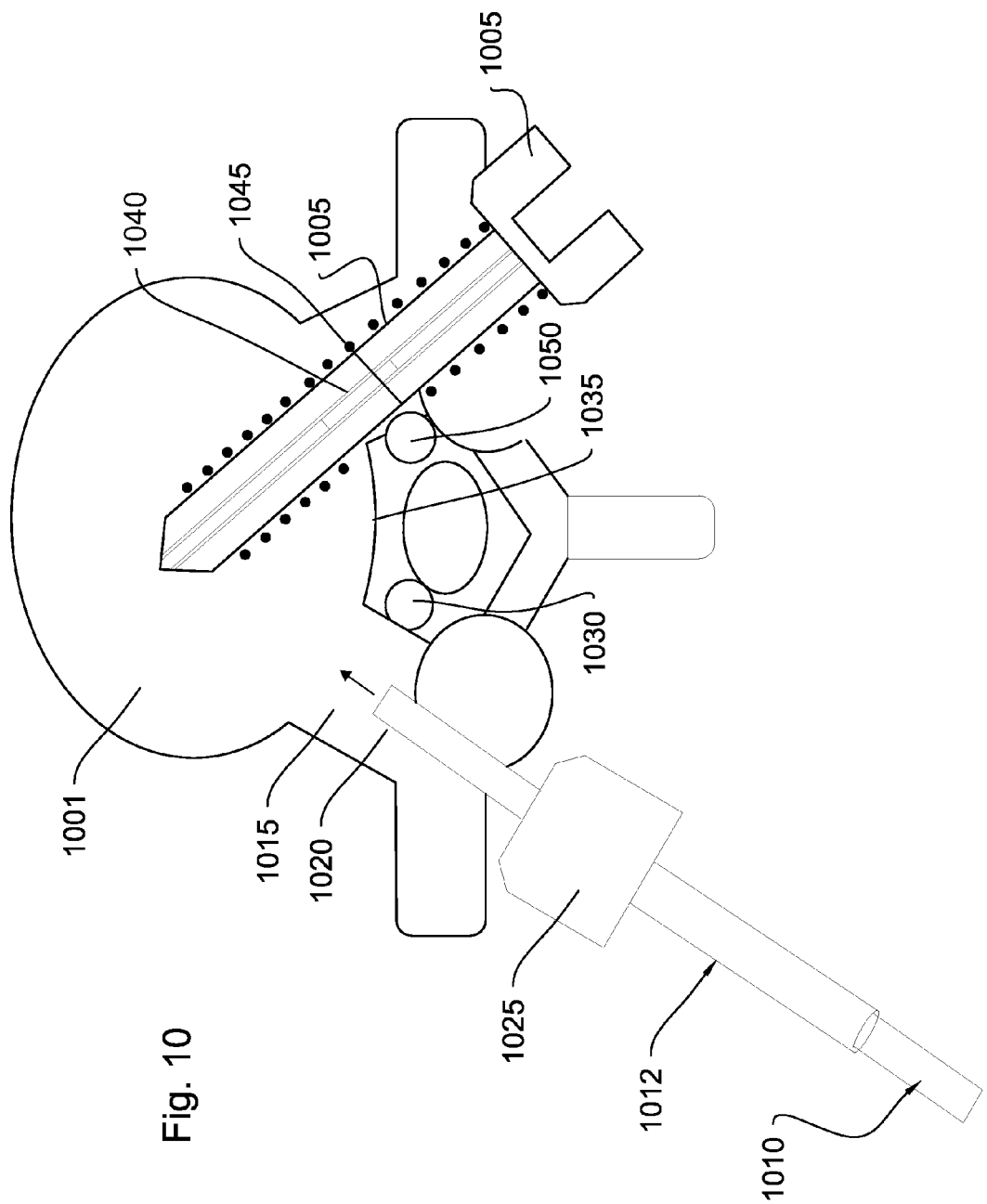
FIG. 10 is a cross sectional view of an exemplary vertebra with an exemplary pedicle screw and an exemplary depth gauge in position, in accordance with an embodiment of the present invention.

FIG. 10 is a cross sectional view of an exemplary vertebra 1001 with an exemplary pedicle screw 1005 and an exemplary depth gauge 1010 in position, in accordance with an embodiment of the present invention. In typical use of the present embodiment, a surgeon may cannulate a pedicle 1015 of vertebra 1001 in any manner he chooses. Then, gauge inner sleeve 1010 is passed over a wire inserted into the pedicle 1015. This portion of the gauge 1010 may incorporate a tap at the end for ease of use. The gauge 1010 is advanced, for example by tapping, until the tapered tip 1020 of gauge 1010 has advanced to the location of the nerve root. The presumed position of nerve root 1030 is just posterior to the junction of the pedicle 1015 and the posterior wall 1035 of the vertebral body. This relationship is confirmed by lateral fluoroscopic imaging or other imaging criteria. With tip 1020 maintained in proper position adjacent to the nerve root, the outer sleeve of the depth gauge 1012 is advanced until the pedicle screw head shaped end 1025 contacts the bone or until the desired installed location of the pedicle screw head 1025 is reached.

With the tip 1020 in proper position and the outer sleeve 1012 fully advanced to the bone, a measurement can be taken. The length is read from a scale contained on the exposed end of gauge 1010. The reading is taken from the end of the outer sleeve 1012. A pedicle screw corresponding to this measurement is selected. Gauge 1010 is then removed from pedicle 1015 and the selected screw is inserted into the cavity in pedicle 1015. Validation of the screw length is typically made fluoroscopically after insertion. For example, without limitation, a marker 1040 in pedicle screw 1005 may be visualized fluoroscopically to generally ensure that a non-threaded portion 1045 of screw 1005 spans the location of a nerve root 1050. Various different types of markers may be used to validate the length of the screw including, without limitation, internal integrated markers, external integrated markers, or removable markers.

Presently, depth gauges are sometimes used in orthopedic and spine surgery to obtain measurements such as, but not limited to, the length of the pedicle. In the present embodiment, the measurement obtained by gauge 1010 is neither the length of pedicle 1015 nor the distance from nerve root 1030 to the bone edge of vertebra 1001. Rather, the measurement obtained by gauge 1010 closely approximates the distance from nerve root 1030 to the bottom of the pedicle screw head after screw placement. This generally enables the surgeon to select the proper screw length to place the non-threaded portion of the pedicle screw such that it spans the location of the nerve root. This typically decreases the risk of interaction between the often sharp threading of the pedicle screw and the sensitive nerve root.

In some alternate embodiments, gauges may be implemented that place a marker into a position that corresponds to the marker inserted into the pedicle screw during insertion. In other alternate embodiments, gauges may comprise a marker on a wire that is inserted into a conduit until the marker is aligned with the assumed nerve root. The wire in these embodiments may be marked with measurement indicators to enable a user to measure the depth of the marker to approximate the depth of the assumed nerve root.

All the features disclosed in this specification, including any accompanying abstract and drawings, may be replaced by alternative features serving the same, equivalent or similar purpose, unless expressly stated otherwise. Thus, unless expressly stated otherwise, each feature disclosed is one example only of a generic series of equivalent or similar features.

Having fully described at least one embodiment of the present invention, other equivalent or alternative methods of providing a pedicle screw system according to the present invention will be apparent to those skilled in the art. The invention has been described above by way of illustration, and the specific embodiments disclosed are not intended to limit the invention to the particular forms disclosed. For example, the particular implementation of the depth gauge may vary depending upon the particular type of inner conduit used. The inner conduits described in the foregoing were directed to sliding implementations; however, similar techniques are to include, without limitation, inner conduits that are stationary or move in various different manners. For example, without limitation, one alternate embodiment may comprise a threaded inner conduit that is advanced by screwing into or out of the outer housing. Non-sliding implementations of the present invention are contemplated as within the scope of the present invention. The invention is thus to cover all modifications, equivalents, and alternatives falling within the spirit and scope of the following claims.

Claim elements and steps herein may have been numbered and/or lettered solely as an aid in readability and understanding. Any such numbering and lettering in itself is not intended to and should not be taken to indicate the ordering of elements and/or steps in the claims.

What is claimed is:

1. A method for measuring a pedicle depth comprising the steps of:
    preparing a cannulation in a patient's pedicle;
    inserting a radiographically distinguishable marker into the cannulation, the marker being disposed at a distal end of an inner member being configured for slidable movement within an outer tubular member comprising a head member being configured to slidably pass the distal end of the inner member;
    fluoroscopically observing placement of the marker proximate the patient's nerve root;
    sliding the outer tubular member to contact the head member to the patient's pedicle; and
    reading an indicator member indicating a distance between the contact surface of the head member and the marker, in which the distance is used to choose a size of a pedicle screw for mitigating damage to the patient's nerve root upon insertion of the pedicle screw into the cannulation.

2. The method for measuring a pedicle depth as recited in claim 1, further comprising the step of tapping an end of the inner member opposing the distal end to assist in inserting the marker.

3. The method for measuring a pedicle depth as recited in claim 1, in which the head member is configured to resemble the head of a pedicle screw.

4. The method for measuring a pedicle depth as recited in claim 1, in which the marker comprises a length corresponding to a length of a non-threaded middle portion of the pedicle screw.

* * * * *

UNITED STATES PATENT AND TRADEMARK OFFICE
CERTIFICATE OF CORRECTION

PATENT NO. : 8,986,318 B2
APPLICATION NO. : 13/427865
DATED : March 24, 2015
INVENTOR(S) : Smith Page 1 of 1

It is certified that error appears in the above-identified patent and that said Letters Patent is hereby corrected as shown below:

In the specification

<u>Column 1</u>
Delete Paragraph [001], Lines 6-15, and replace with -- The present utility patent application is a continuation-in-part application of U.S. Patent Application No. 13/427,841, filed March 22, 2012, which is a continuation-in-part application of U.S. Patent Application No. 12/132,476, filed June 3, 2008 now U.S. Patent No. 8,740,956, both under 35 U.S.C. 111(a). The contents of these related utility patent applications are incorporated herein by reference for all purposes to the extent that such subject matter is not inconsistent herewith or limiting hereof. --

Signed and Sealed this
Twentieth Day of October, 2015

Michelle K. Lee
*Director of the United States Patent and Trademark Office*